United States Patent [19]
Kugel

[11] Patent Number: 5,769,864
[45] Date of Patent: Jun. 23, 1998

[54] HERNIA MESH PATCH

[75] Inventor: Robert D. Kugel, Olympia, Wash.

[73] Assignee: Surgical Sense, Inc.

[21] Appl. No.: 755,108

[22] Filed: Nov. 22, 1996

Related U.S. Application Data

[63] Continuation-in-part of Ser. No. 315,249, Sep. 29, 1994, Pat. No. 5,634,931.
[51] Int. Cl.[6] .................................................. A61B 17/04
[52] U.S. Cl. .............................................. 606/151; 602/44
[58] Field of Search ........................... 606/151, 213–215, 606/110, 113; 602/44, 58

[56] References Cited

U.S. PATENT DOCUMENTS

| | | |
|---|---|---|
| 2,671,444 | 3/1954 | Pease, Jr. . |
| 3,054,406 | 9/1962 | Usher . |
| 4,347,847 | 9/1982 | Usher . |
| 4,452,245 | 6/1984 | Usher . |
| 4,561,434 | 12/1985 | Taylor . |
| 4,854,316 | 8/1989 | Davis . |
| 5,059,205 | 10/1991 | El-Nounou et al. . |
| 5,116,357 | 5/1992 | Eberbach . |
| 5,122,155 | 6/1992 | Eberbach . |
| 5,141,515 | 8/1992 | Eberbach . |
| 5,147,374 | 9/1992 | Fernandez . |
| 5,147,384 | 9/1992 | La Rocca . |
| 5,254,133 | 10/1993 | Seid . |
| 5,258,000 | 11/1993 | Gianturco . |
| 5,290,217 | 3/1994 | Campos . |
| 5,318,559 | 6/1994 | Mulhauser . |
| 5,356,432 | 10/1994 | Rutkow et al. . |
| 5,370,650 | 12/1994 | Tovey et al. . |

FOREIGN PATENT DOCUMENTS

WO 94/27535  12/1994  WIPO .

*Primary Examiner*—Gary Jackson
*Attorney, Agent, or Firm*—James E. Bradley

[57] ABSTRACT

A hernia patch has a first layer of inert synthetic mesh material selectively sized and shaped to extend across and beyond a hernia. A second layer of inert synthetic mesh material overlies the first layer to create a generally planar configuration for the patch. The first and second layers are joined together by a seam which defines a periphery of a pouch between the layers. One of the layers has a border which extends beyond the seam and which has a free outer edge. A plurality of border slits extend from the outer edge through the border substantially to the seam. An access slit is formed in one of the layers for insertion of a finger of a surgeon into the pouch to allow the surgeon to deform the planar configuration of the patch to facilitate insertion of the patch into the patient and to position the patch across the hernia. A resilient monofilament loop is located within and surrounds the pouch at the seam for urging the patch to conform to the generally planar configuration across the hernia as the surgeon withdraws his or her finger.

14 Claims, 3 Drawing Sheets

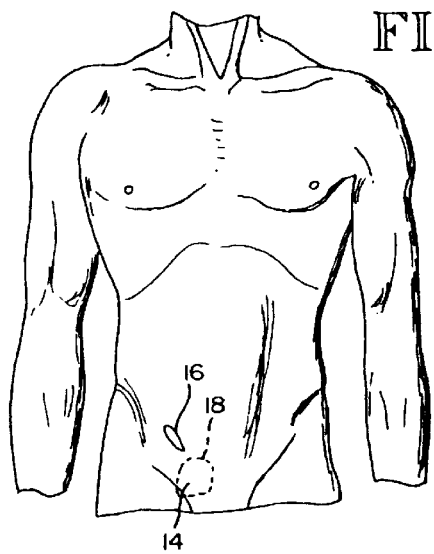
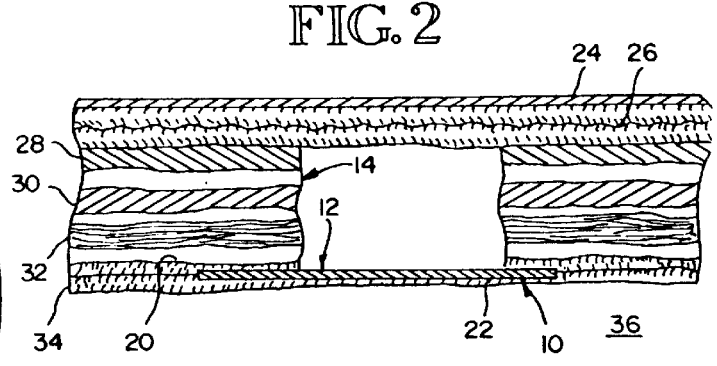
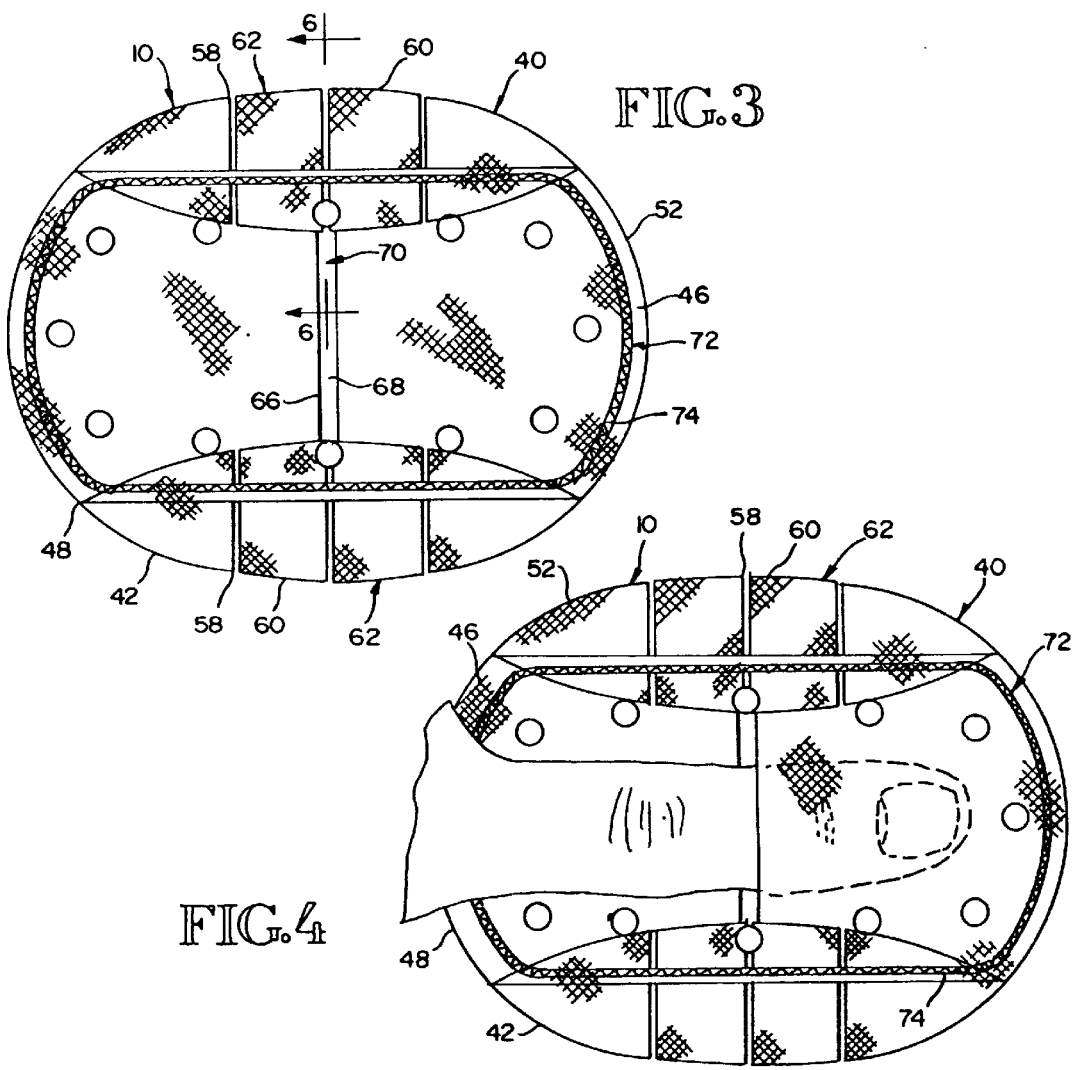

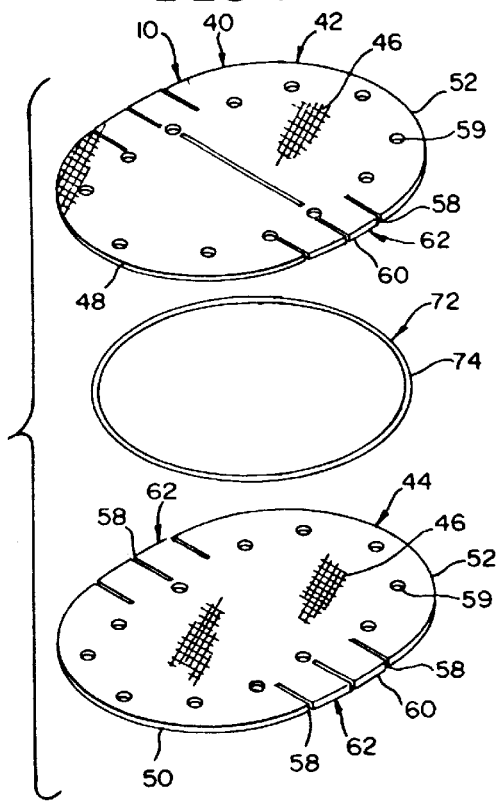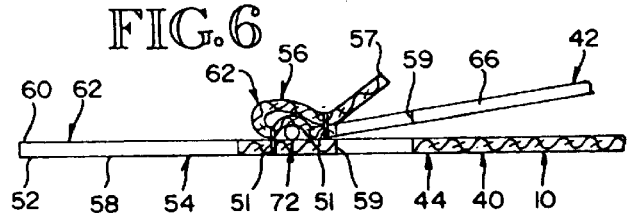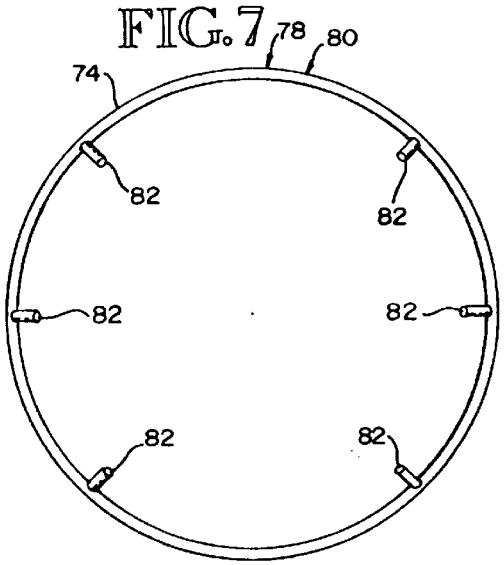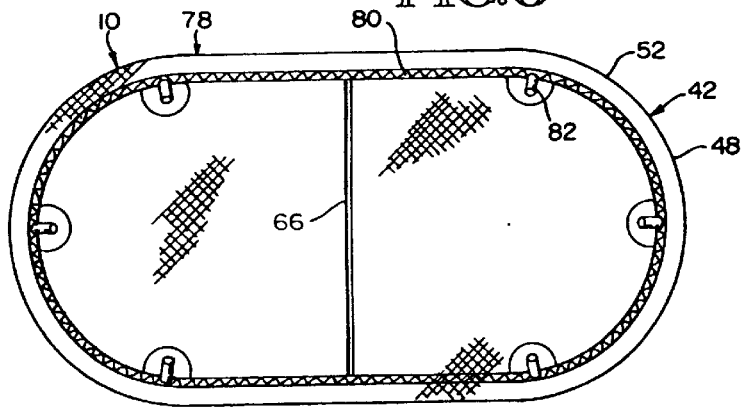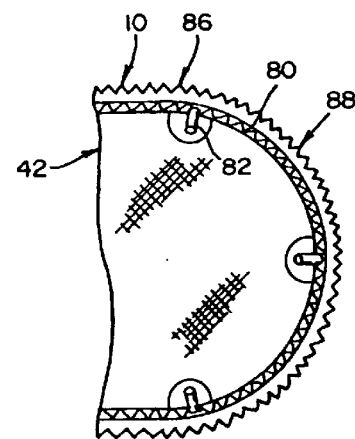

HERNIA MESH PATCH

This application is a continuation-in-part of application Ser. No. 08/315,249, filed Sep. 29, 1994, now U.S. Pat. No. 5,634,931, Hernia Mesh Patches and Methods of Their Use.

TECHNICAL FIELD

Surgically implantable mesh patches for the repair of inguinal and other abdominal wall hernias, which are intended for permanent placement within a patient's body space, have been provided and used previously. Tension free surgical repairs of hernias have been developed using synthetic mesh materials to bridge and to patch hernia defects. These repairs resulted in both a decrease in the recurrence rate as well as a decrease in the amount of a patient's post operative discomfort. Patients undergoing these more advanced procedures were able and are able to resume their normal activities sooner.

Some of these earlier techniques are somewhat complicated. Several use a plug or a locating member to fit within the hernia defect itself. Also many of these earlier techniques were designed specifically for use in laparoscopic repair of hernias. Moreover, many of the prior inventions required suturing to the patient's body tissue. Although these medical advances are acknowledged for their usefulness and success, there remained a need or needs for more improvements in the surgical repair of hernias.

DISCLOSURE OF INVENTION

A hernia mesh patch for use in the surgical repair of a patient's inguinal, or other abdominal wall hernias, is disclosed for permanent placement within a patient's body space. This hernia mesh patch has top and bottom layers of an inert, synthetic mesh, preferably polypropylene mesh, secured to each other with a seam. The seam surrounds and defines a pocket. The top layer has a transverse cut or slit opening into the interior pocket or pouch volume of this patch.

To serve a spring function, an implantable inert monofilament fiber, arranged in an oval, ovoid, loop, or ring configuration, having a circumference slightly greater than the circumference of the interior pocket volume of this patch, is inserted into this pocket to keep the hernia mesh patch expanded under tension in a planar configuration. A border on at least one of the layers extends outward past the seam. The border preferably has slits to fill uneven voids in the patient's tissue and fit more tightly.

Without the need for general anesthesia, nor expensive laparoscopic instrumentation, a surgeon, when repairing an inguinal hernia, makes a small incision in the patient, approximately three centimeters long, arranged obliquely, approximately two to three centimeters above the internal ring location of the inguinal hernia. Through this small incision, using the muscle splitting technique, the surgeon performs a dissection deep into the patient's properitoneal space, creating a pocket in this space into which this hernia mesh patch is to be inserted.

Thereafter, the surgeon, using his or her fingers, readily folds and compacts this hernia mesh patch and directs it through the incision and into the patient's properitoneal space, where it unfolds and expands into its planar configuration, creating a trampoline effect. Then the surgeon, using just one of his or her fingers, placed partially through a slit in the top layer of mesh and into the pocket between the top and bottom layers of this hernia mesh patch, conveniently and accurately moves the hernia mesh patch to cover the defect in the patient's thick reinforcing lining of his or her abdominal cavity. Thereafter the surgeon withdraws his or her finger and then secures the incision with stitches.

The patient's body, soon after surgery, reacts to the mesh of the hernia mesh patch, and in a short time, the mesh becomes stuck, thereby keeping the hernia mesh patch in place. Thereafter the patient's scar tissue grows into the mesh over a period of time, between thirty and sixty days, to permanently fix the hernia mesh patch in its intended position over the repaired area, where the hernia was located.

In respective designs of these hernia mesh patches, small holes are cut through both layers of the mesh inside the fiber ring, to increase friction and to minimize the sliding or migration of the hernia mesh patch, after it is positioned. Also in some designs, spaced spikes are attached to the fiber spring, or are integrally formed with the fiber spring to serve as anchors, by entering the patient's tissue. Also in some designs of these hernia mesh patches to be used in a location where the patient's peritoneum has been destroyed, one layer of this patient's hernia patch is made of a material, such as "Gortex" material, which is less prone to adhere to a bowel or other intra-abdominal organ.

BRIEF DESCRIPTION OF DRAWINGS

FIG. 1 is a schematic partial front view of a patient's body indicating, in respect to the surgical repair of an inguinal hernia, where a three centimeter incision is made obliquely approximately two to three centimeters above the location described as the internal ring of the hernia, in reference to the location of an inguinal hernia.

FIG. 2 is a schematic partial diagrammatic cross-sectional view of a patient's abdominal wall layers showing an inguinal or other abdominal wall hernia, and where the surgically implantable hernia repair mesh patch has been correctly positioned in the properitoneal created space.

FIG. 3 is a top view of a preferred embodiment of the surgically implantable hernia repair mesh patch, having anchoring or friction holes cut through both layers of the mesh, which after the surgical insertion of the surgically implantable hernia repair mesh patch, serve to minimize any risk of the mesh migrating or moving once positioned by a surgeon.

FIG. 4 is similar to FIG. 3, showing how a surgeon's finger is inserted through a slit, which is made by cutting through only the top layer of the two layers of mesh used in this surgical hernia patch, whereby a surgeon's finger, so inserted between these layers of mesh, then directs the movement of this surgical hernia patch through the incision and on to the location of the inguinal hernia.

FIG. 5 is an exploded view of the surgically hernia repair mesh patch shown in FIGS. 2, 3 and 4, to show the two layers of the mesh, preferably cut from polypropylene mesh material, and also to show a resilient monofilament ring, which when located between the layers of mesh, becomes a resilient spring ring keeping the surgical hernia patch fully expanded.

FIG. 6 is a transverse cross sectional view of the center of the preferred surgically implantable hernia repair mesh patch, illustrated in FIGS. 2, 3, 4 and 5, with the top and bottom layers shown slightly separated for illustrative purpose.

FIG. 7 is a top view of another resilient monofilament ring, which becomes the located spring ring, showing how spaced anchoring monofilament spikes are secured to this ring or are made integral with this ring or are made integral with this ring;

FIG. 8 is a top view of a second embodiment of the surgically implantable hernia repair mesh patch.

FIG. 9 is a partial top view of a third embodiment illustrating a circular surgically implantable hernia repair mesh patch.

BEST MODE FOR CARRYING OUT THE INVENTION

Figure 10:
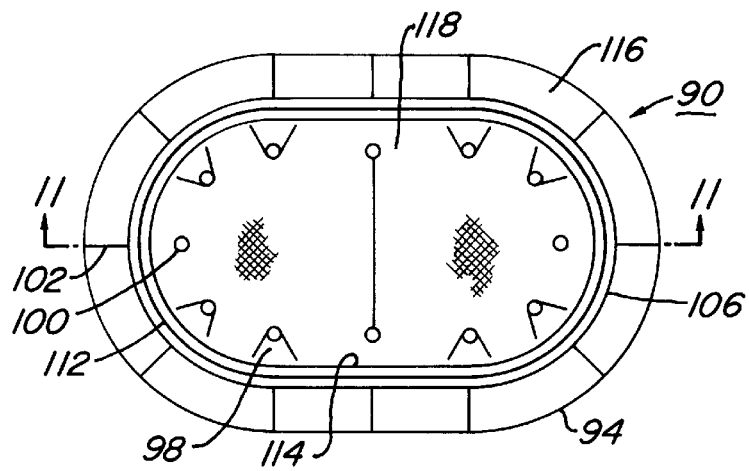
FIG. 10 is a plan view of a fourth embodiment of a patch constructed in accordance with this invention.

The hernia mesh patches 10, illustrated in the drawings, are surgically permanently implantable within a patient's body space 12 to adequately cover, correct, prevent and repair any inguinal or other abdominal wall hernias 14 or other types of hernias. The surgeon has the objective of making a sutureless repair, by first cutting an approximately three centimeter incision 16, obliquely positioned approximately two to three centimeters above the location described as the internal ring 18, where an inguinal hernia 14 has occurred, as shown in FIG. 1. Then the surgeon working through this incision 16, and using a muscle splitting technique, dissects deeply into the patient's properitoneal space 20, entering slightly superior and posterior to the patient's hernia defect 14. The surgeon then creates a pocket 22 in the patient's properitoneal space 20, into which the hernia mesh patch 10 is inserted, as shown in FIG. 2.

The surgeon in dissecting deeply into the patient's properitoneal space 20, as indicated in FIG. 2, will have used a sharp instrument to make the incision or wound 16 through the patient's skin 24, the subcutaneous fatty tissues 26, and the external oblique fascia 28, which has been cut parallel with its fibers a short distance. Then the surgeon has incised the transversalis fascia 32, creating an entrance into the properitoneal space 20, above the peritoneum 34 at a location superior to the hernia 14. In so doing, the surgeon has identified and freed up the hernia sac and has created the pocket 22 in the properitoneal space 20. This space 20 underlies the area referred to as Hesselbach's triangle, in reference to both indirect and direct hernias. The surgeon's placement of this hernia mesh patch 10, using this method, protects the entire inguinal floor, and therefore not only will it repair or correct a single small hernia, but will also protect against future hernias through other potentially weakened areas. In a similar way, a hernia mesh patch 10, sandwiched between a hernia 14, i.e. defect 14, and the inner lining 34, i.e. the peritoneum 34, of the abdominal cavity 36, is used to underlay a femoral canal area, not shown, through which femoral hernias occasionally occur. Wherever used, the hernia mesh patch 10, in its respective embodiments, serves as the basis for tension free surgical repair of a hernia, as it is used to patch and to bridge the hernia 14, i.e. the defect 14. The hernia mesh patch 10 is made, so after completing this preparation, the surgeon using his or her fingers, can fold and compact the hernia mesh patch 10 and insert it down through the incision 16 into properitoneal space 20. Thereafter, using his or her finger, the surgeon expands, moves, and directs, the hernia mesh patch 10 into position in the pocket 20 within the properitoneal space 20 to bridge the hernia 14, or defect 14.

An embodiment 40 of these hernia mesh patches 10, is illustrated in FIGS. 2 through 6, which is particularly designed for the repair of an inguinal hernia 10 but also can be used for other abdominal wall hernias. This embodiment 40 is composed of two similarly sized and shaped pieces 42, 44, of an inert synthetic mesh material 46, which preferably is a polypropylene material. This mesh material 46 is formed from monofilament material which is resistant to infection, and which has been used safely in many hernia operations, in previous ways and in previous embodiments. Preferably, the two similarly sized and shaped pieces of mesh material 42, 44 are made in respective circle, loop, ovoid, or oval shapes. One of these pieces 42, 44, is referred to as the first or top layer 42 of the synthetic mesh material 46 and the other one of these pieces 42, 44, is referred to as the second or bottom layer 44 of the synthetic mesh material 46. These two layers 42, 44, are secured to each other by sewing in the first three embodiments and by sonic welding in the last embodiment. In the first three embodiments, the seam is approximately one centimeter in from their outer edges 48, 50 using a thread 51 of inert synthetic material. The outer one centimeter of mesh material 52 of the bottom mesh material piece or layer 44 is left free to serve as a border or apron 54 to fill uneven voids in the patient's tissue. The outer one centimeter of mesh material 52 of the top mesh material piece or layer 42 is folded back and sewn adjacent the fold 56, while leaving free the remaining portions of this outer one centimeter of mesh material 52 of this top mesh layer 42. Thereafter, this free portion 57, when the hernia mesh patch 10 has been placed in the properitoneal space, serves to frictionally keep this patch 10 in its hernia 14 repair position. Also inside of the fold 56, like size holes 59, aligned one above the other, are cut respectively in the top and bottom mesh layers 42, 44. The presence of these holes 59 helps initially to frictionally keep the hernia mesh patch 10 in place. Thereafter the patient's scar tissues grow in and around these holes 59 to continue to keep the hernia mesh patch in position. The outer one centimeter of mesh materials 52 are both cut or slit 58, radially or diagonally creating scalloped or fringed edges 60, or tab portions 62, of both the outer one centimeter of mesh materials 52, of the top and bottom mesh layers 42, 44.

Also the top mesh material, or top layer piece 42, is cut or slit 66 transversely at the center 68 thereof, creating a finger access 66 into the interior space 70, or pouch 70, between the top and bottom layers 42, 44 of the synthetic mesh material 46. Through this slit 66, a ring like arrangement 72 of a continuous, inert, implantable, monofilament fiber 74, when squeezed temporarily to narrow it and to elongate it, is inserted into the interior space 70 or pouch 70. Then it is released, and allowed to expand, serving a spring function and therefore it is called a spring 72, while it is compressibly held in this interior space 70 or pouch 70 of the hernia mesh patch 10, thereby keeping this patch 10 fully extended in a planar arrangement, as shown in FIGS. 2, 3, and 4. This spring 72 is made of a synthetic material, such as nylon, polypropylene, or polyester. In each embodiment, this monofilament loop, ring or spring 72, has a circumference which is slightly larger than the circumference of the interior space 70, or pocket 70, or pouch 70, which is formed between the top and bottom layers 42, 44 of the synthetic mesh material 46.

A second embodiment 78 is illustrated in FIGS. 7 and 8, wherein the ring or spring 80 has spaced monofilament spikes 82 secured to the ring 80, or made integrally with it.

They are directed on an angle to extend above this embodiment 78 of a hernia mesh patch 10, to enter the patient's body tissue. In this way the continuing accurate location of this hernia mesh patch 10 is insured. The outer one centimeter of mesh material 52, as shown in FIG. 8, is not cut nor slit.

A third embodiment 86 is illustrated in FIG. 9, wherein a portion of it is shown, indicating its similarity to the second embodiment 78, illustrated in FIGS. 7 and 8. However, the outer one centimeter of mesh materials 52 are cut to create scalloped or fringed circumferential edges 88, above and below, which also serve to frictionally hold the hernia mesh patch 10 in place, along with the spikes 82 on the loop, ring or spring 80.

Figure 11:
FIG. 11 is a sectional view of the patch of FIG. 10, taken along the line 11—11 of FIG. 10.
Figure 12:
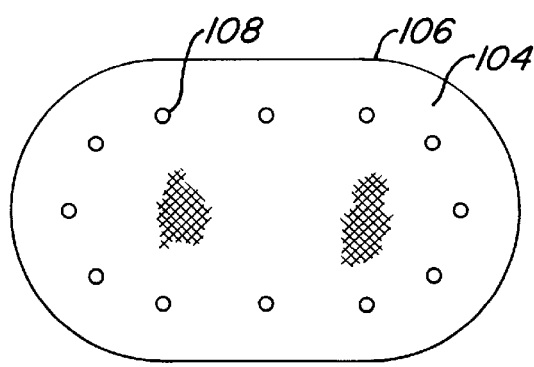
FIG. 12 is a plan view of one of the layers of the patch of FIG. 10.
Figure 13:
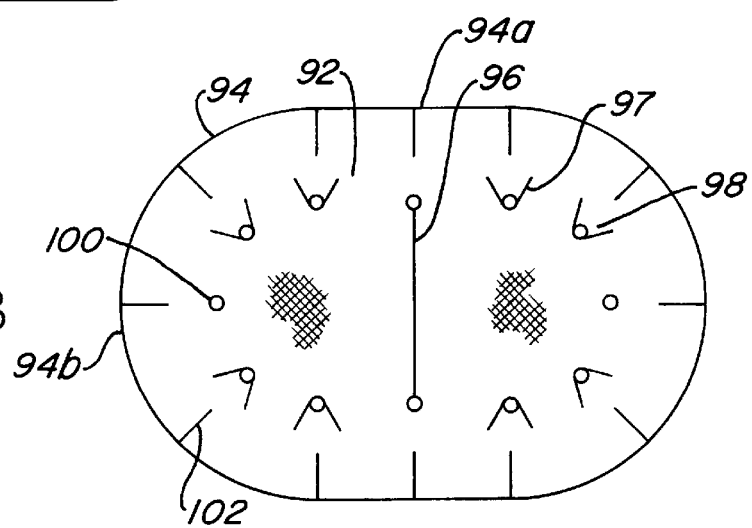
FIG. 13 is a plan view of the other of the layers of the patch of FIG. 10.

A fourth embodiment 90 of a patch 10 is shown in FIGS. 10–13. Patch 90 has a first layer 92 of an inert synthetic mesh material. Layer 92, as shown in FIG. 13, has an outer edge 94 that in the embodiment shown is generally oval, having straight sides 94a and curved ends 94b. An access slit 96 extends in a straight line transversely across a portion of layer 92, perpendicular to straight sides 94a. Slit 96 is large enough to accommodate a finger of a surgeon. In addition, a plurality of dart-shaped slits 97 are formed in layer 92. Dart slits 97 define a dart or triangular shaped tab 98 which pops or protrudes up from layer 92. Dart tabs 98 are oriented in a generally oval array similar to outer edge 94, but spaced inwardly. Four of the dart tabs 98 are located inward from each curved end 94b. In addition, a circular hole 100 is located at the center point but inward from each curved end 94b.

A plurality of border slits 102 extend inward from each outer edge 94. Each border slit 102 is a straight line. The border slits 102 are located outward from dart tabs 98 and holes 100. In the embodiment shown, there are three border slits 102 leading inward from each straight side 94a and three evenly spaced border slits 102 leading inward from each curved end 94b.

Referring to FIG. 12, second layer 104 has a similar oval configuration, however is smaller in size. Second layer 104 is also an inert mesh synthetic material having a generally oval-shaped edge 106. A plurality of holes 108 are located in layer 104. Each hole 108 is circular and spaced in an oval pattern, but inward from outer edge 106. Holes 108 are evenly spaced and aligned with the holes 100 and dart tabs 98 of layer 92 when assembled together as shown in FIG. 10. Dart tabs 98 and holes 100, 108 result in openings extending completely through patch 90.

Referring to FIG. 11, a resilient loop 110 of a monofilament fiber locates between the two layers 92, 104. Once installed, loop 110 is preferably generally oval-shaped. Loop 110 is located outward of holes 108 and slightly inward of outer edge 106 of layer 104. Once assembled as shown in FIG. 11, two seams 112, 114 are formed to join layers 92, 104 together. Seam 114 is located slightly inward of loop 110, while seam 112 is located slightly outward of loop 110. Seams 112, 114 are preferably formed by conventional sonic welding techniques.

Seams 112, 114 are located inward from outer edge 94 of layer 92, creating a border 116. Seams 112, 114 are also located slightly inward of border slits 102. As shown in FIG. 10, seams 112, 114 define a pocket or pouch 118 between layers 92, 104. Access slit 96 serves as access to pouch 118. Loop 110 is located at the periphery of pouch 118 and urges patch 90 to a flat configuration. This configuration may be deformed during the insertion and placement of patch 90. Loop 110 causes dart tabs 98 to pop up and protrude from the surface of layer 92. Dart tabs 98 tend to grab tissue when patch 90 is implanted to hold patch 90 in place without the need for sutures.

In use, at the conclusion of the surgeon's use of both sharp and blunt instruments to create pocket 22 in the properitoneal space 20, he or she selects the type and size embodiment of the hernia mesh patch 10 best suited to be used in the repair of the patient's defect or hernia 14. The selected embodiment 40, 78, 86, 90 or another one, not shown, of the hernia mesh patch 10, is folded and further compacted, as may be necessary, by the surgeon using his or her fingers, so the selected patch 10 may be conveniently inserted through the wound or incision 16 and down into the properitoneal space 20. Referring to the first embodiment, shown in FIG. 3, in this space 20, the hernia mesh patch 10 is freed and allowed to expand under the force of the loop 74. Thereafter the surgeon using his or her finger, continues any further expansion of this patch 10, which might be necessary. Then his or her finger is inserted through the cut or slit 66 in the center 68 of the top mesh layer 42, and the hernia mesh patch 10 through the properitoneal space to the pocket 22. After the withdrawal of his or her finger, the surgeon completes the repair surgery by closing the wound or incision with stitches, in respect to this repair of an inguinal hernia, using the remote incision 16, as illustrated in FIG. 1.

In the repair of other hernias, and especially those that are large, a direct incision is made, and after the placement of a large hernia mesh patch 10, the surgeon may use limited sutures to keep the larger hernia mesh patch 10 in place. Generally, most of the embodiments of this hernia mesh patch 10 are positioned, and so remain, without the use of sutures.

In respect to the utilization of all of the embodiments of these hernia mesh patches 10, they have their simplicity of manufacturing design and of their surgical method of insertion. All these patches 10 adequately underlay a hernia 14 or defect 14, with a minimum of two centimeters of a surrounding underlay about the circumference of the hernia 14. They do so, with sufficient rigidity and with sufficient friction, to eliminate or minimize sliding or migration. When these hernia mesh patches 10 are used by a surgeon, the repair of a patient's inguinal hernia 14, or of another abdominal wall hernia 14, is repaired through a smaller wound or incision 16, with less surgical tension, less postoperative patient discomfort, shorter operation time, and at a potential lower cost to the patient.

The hernia mesh patches are made in several sizes. Four standard sizes accommodate ninety percent of the inguinal and abdominal wall hernias. With respect to repairing inguinal hernias, the most appropriate size is eight by twelve centimeters. The diameter of the monofilament fiber, which is preferably made from nylon, polypropylene, or polyester, and arranged to subsequently serve as a spring, is adjusted in size in respect to the selected size of the hernia mesh patch to be used. A larger diameter fiber is used in the spring of a larger diameter mesh patch to make the hernia mesh patch stiffer. While allowing for the sufficient stiffness to insure the hernia mesh patch will open to its predetermined overall dimensions, there must be adequate flexibility to allow this hernia mesh patch to conform to the patient's uneven body contours and surfaces, and initially to allow for the folding and compacting of the hernia mesh patch for its insertion through the small entrance incision. In respect to all sizes of these hernia mesh patches, the presence of the monofilament fiber spring also allows for the use of a smaller diameter mesh fiber, which might otherwise be necessary to provide the necessary stiffness in a patch not having such a fiber spring.

In respect to large hernia mesh patches, the spring may include the winding of two or more monofilament fibers. Also large hernia mesh patches are initially kept from sliding by using a limited number of anchoring stitches. They are placed without creating tension, without significantly increasing a patient's post-operative discomfort, and without contributing to the strength of the overall surgical repair of the patient's hernia.

Regarding the free outer edges of the respective top and bottom layers of the mesh material, they are slit in radial cuts to create scalloped or fringed edges. The bottom layer flat scalloped edges serve to fill uneven voids in the patient's tissue surface, which helps to minimize any risk of the patient's tissue slipping over this patch and allowing the hernia to recur. The top scalloped edges are folded back and sewn along the monofilament fiber spring, leaving some portions of their folded over scalloped edges free to subsequently resist the migration of this hernia mesh patch, after it has been inserted into the limited sized properitoneal pocket or pouch developed by the surgeon under the patient's hernia defect. The hernia mesh patch held in its intended shape by the fiber spring completely fills enough of this pocket to completely extend over and beyond the patient's hernia defect. After its initial insertion, and thereafter, the patient's hernia mesh patch is held in position by the hydrostatic pressures created between the two tissue layers of fascia above the patch and the peritoneum below the patch.

In respect to all the hernia mesh patches, they have their simplicity of design and method of insertion. They adequately underlay a hernia defect by a minimum of two centimeters around the circumference of the hernia defect, with sufficient rigidity and with sufficient friction to eliminate or minimize sliding or migration. When these hernia mesh patches are used, the repair of inguinal and other abdominal wall hernias are repaired through a smaller wound or incision, with less tension, less post-operative discomfort, shorter operating time, and at a potential lower cost to the patient. The patient's post-operative discomfort is decreased, and risk of any recurrence is likewise decreased.

While the invention has been shown in several embodiments, it should be apparent that it is not limited to those embodiments but is susceptible to various changes without departing from the scope of the invention.

I claim:

1. A hernia patch, comprising:

a first layer of inert synthetic mesh material sized and shaped to extend across and beyond a hernia;

a second layer of inert synthetic mesh material;

securing means for securing the first and second layers to each other to create a pouch between the first and second layers;

a slit in one of the layers for insertion of a finger into the pouch to position the patch across the hernia; and a resilient loop adjacent a periphery of the pouch for creating tension in both of the layers.

2. The patch according to claim 1, further comprising:

a plurality of dart-shaped slits formed in one of the layers in a portion forming a part of the pouch, defining dart-shaped tabs which protrude from said one of the layers to engage tissue of a patient for retaining the patch in place.

3. The patch according to claim 1 wherein:

the securing means is a seam extending around the periphery of the pouch; and one of the layers has a border which extends beyond the seam to fill uneven voids in a patient's tissue.

4. The patch according to claim 1 wherein:

the securing means is a seam extending around the periphery of the pouch;

one of the layers has a border which extends beyond the seam and which has a free outer edge; and the border has a plurality of slits extending inward from the outer edge to fill uneven voids in a patient's tissue.

5. The patch according to claim 1 wherein:

the securing means is a seam extending around the periphery of the pouch;

one of the layers has a border which extends beyond the seam and which has a free outer edge;

the border has a plurality of slits extending inward from the outer edge to fill uneven voids in a patient's tissue; and one of the layers has a plurality of dart-shaped slits inward from the seam, creating dart-shaped tabs which protrude from said one of the layers to engage tissue to retain the patch.

6. The patch according to claim 1 wherein:

the loop is a monofilament fiber located within the pouch at the periphery of the pouch.

7. A hernia patch, comprising:

a first layer of inert synthetic mesh material sized and shaped to extend across and beyond a hernia;

a second layer of inert synthetic mesh material overlying the first layer to create a generally planar configuration for the patch;

the first and second layers being joined together by a seam which defines a periphery of a pouch between the layers;

a slit in one of the layers for insertion of a finger of a surgeon into the pouch to facilitate insertion of the patch into the patient and to position the patch across the hernia; and a resilient loop located within the pouch and adjacent to the seam for urging the patch to conform to the generally planar configuration across the hernia as the surgeon withdraws his or her finger.

8. The patch according to claim 7, further comprising:

a plurality of dart-shaped slits formed in one of the layers in a portion forming a part of the pouch, the dart-shaped slits defining dart-shaped tabs which protrude from said one of the layers to engage tissue for retaining the patch.

9. The patch according to claim 7 wherein one of the layers has a border which extends beyond the seam and has a free outer edge.

10. The patch according to claim 7 wherein:

one of the layers has a border which extends beyond the seam and which has a free outer edge; and the border has a plurality of slits extending inward from the outer edge to fill uneven voids in a patient's tissue.

11. The patch according to claim 7 wherein:

one of the layers has a border which extends beyond the seam and which has a free outer edge;

the border has a plurality of slits extending inward from the outer edge to fill uneven voids in a patient's tissue; and a plurality of dart-shaped slits are formed in one of the layers in a portion forming a part of the pouch, the dart-shaped slits defining dart-shaped tabs which protrude from said one of the layers to enhance retaining the patch in place.

12. The patch according to claim 7 wherein the loop is a monofilament fiber.

13. A hernia patch, comprising:

a first layer of inert synthetic mesh material sized and shaped to extend across and beyond a hernia;

a second layer of inert synthetic mesh material overlying the first layer to create a generally planar configuration for the patch;

the first and second layers being joined together by a seam which defines a periphery of a pouch between the layers;

one of the layers having a border which extends beyond the seam and which has a free outer edge;

a plurality of border slits extending from the outer edge through the border substantially to the seam;

an access slit in one of the layers for insertion of a finger of a surgeon into the pouch to facilitate insertion of the patch into the patient and to position the patch across the hernia; and a resilient monofilament loop located within the pouch at the seam for urging the patch to conform to the generally planar configuration across the hernia as the surgeon withdraws his or her finger.

14. The patch according to claim 13, further comprising:

a plurality of dart-shaped slits formed in one of the layers in a portion forming a part of the pouch, defining dart-shaped tabs which protrude from said one of the layers to enhance retaining the patch in place.

* * * * *